US011179445B2

(12) United States Patent
Park et al.

(10) Patent No.: US 11,179,445 B2
(45) Date of Patent: Nov. 23, 2021

(54) PHARMACEUTICAL COMPOSITION AND BIOMATERIAL COMPRISING FUSION PEPTIDE IN WHICH BONE TISSUE-SELECTIVE PEPTIDE BOUND TO PARATHYROID HORMONE (PTH) OR FRAGMENT THEREOF

(71) Applicants: Nano Intelligent Biomedical Engineering Corporation Co. Ltd., Chungcheongbuk-do (KR); Seoul National University R&DB Foundation, Seoul (KR)

(72) Inventors: Yoon Jeong Park, Seoul (KR); Chong-Pyoung Chung, Seoul (KR); Jue-Yeon Lee, Gyeonggi-do (KR)

(73) Assignees: NANO INTELLIGENT BIOMEDICAL ENGINEERING CORPORATION CO. LTD., Chungcheongbuk-Do (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 80 days.

(21) Appl. No.: 16/326,210

(22) PCT Filed: Nov. 29, 2017

(86) PCT No.: PCT/KR2017/013749
§ 371 (c)(1),
(2) Date: Feb. 17, 2019

(87) PCT Pub. No.: WO2019/066140
PCT Pub. Date: Apr. 4, 2019

(65) Prior Publication Data
US 2020/0113978 A1 Apr. 16, 2020

(30) Foreign Application Priority Data
Sep. 29, 2017 (KR) .................. 10-2017-0126876

(51) Int. Cl.
*A61K 38/00* (2006.01)
*A61K 38/29* (2006.01)
(Continued)

(52) U.S. Cl.
CPC .............. *A61K 38/29* (2013.01); *A61K 35/32* (2013.01); *A61K 38/1709* (2013.01);
(Continued)

(58) Field of Classification Search
CPC .... A61K 38/29; A61K 35/32; A61K 38/1709; A61K 38/39; A61K 47/64; A61K 38/08; A61K 38/10; A61L 2430/02; A61L 27/06; A61L 27/12; A61L 27/24; A61L 27/36; A61L 27/3608; A61L 27/3641; A61L 27/54; A61L 27/56; A61L 27/227; A61P 19/08; A61P 19/10; A61P 19/00;
(Continued)

(56) References Cited

U.S. PATENT DOCUMENTS 6,506,730 B1    1/2003  Lee et al.
8,546,529 B2 *  10/2013 Chung ................... A61L 27/50
                                              530/329
(Continued)

FOREIGN PATENT DOCUMENTS

CN    105924646 B    9/2016
CN    107056794 B    8/2017
(Continued)

OTHER PUBLICATIONS

Baht et al. Bone sialoprotein-collagen interaction promotes hydroxyapatite nucleation. Matrix Biology 27 (2008) 600-608 (Year: 2008).*
Office of the Surgeon General (US). Tommy Thompson. Bone Health and Osteoporosis: A Report of the Surgeon General (Year: 2004).*
Rauch et al. Osteogenesis imperfecta. The Lancet vol. 363, Issue 9418, Apr. 24, 2004, pp. 1377-1385 (Year: 2004).*
Rodan et al. Therapeutic Approaches to Bone Diseases. Science Sep. 1, 2000: vol. 289, Issue 5484, pp. 1508-1514 (Year: 2000).*
Britannica—Bone diseases. Accessed Nov. 12, 2020 at https://www.britannica.com/browse/Bone-Diseases/1 (Year: 2020).*
(Continued)

*Primary Examiner* — James H Alstrum-Acevedo
*Assistant Examiner* — Mercy H Sabila
(74) *Attorney, Agent, or Firm* — Hultquist, PLLC; Steven J. Hultquist

(57) ABSTRACT

The present invention relates to a pharmaceutical composition for preventing or treating bone diseases comprising a fusion peptide in which a bone tissue-selective peptide bound to parathyroid hormone (PTH) or a fragment thereof. More particularly, the present invention relates to a pharmaceutical composition and biomaterial for preventing or treating bone diseases comprising a fusion peptide in which a bone tissue-selective peptide represented by an amino acid sequence of SEQ ID NO. 3 bound to parathyroid hormone (PTH) or a fragment thereof represented by an amino acid sequence of SEQ ID NO. 4 or 5. The fusion peptide can improve effects of PTH by selectively binding to bone tissue and can reduce administration frequency by increasing the half-life. The fusion peptide can be used as a subcutaneous or intravenous injection-type pharmaceutical composition for treating osteoporosis and fracture, and can be used in combination with a medical device for tissue recovery to increase formation of bone tissue. In addition, when the fusion peptide is bound to the surface of dental and orthopedic medical devices, transplantation stability of the medical device can be improved through improved osseointegration between the medical device and new bone.

8 Claims, 4 Drawing Sheets
(3 of 4 Drawing Sheet(s) Filed in Color)
Specification includes a Sequence Listing.

(51) Int. Cl.

| | |
|---|---|
| *A61K 35/32* | (2015.01) |
| *A61K 38/17* | (2006.01) |
| *A61K 38/39* | (2006.01) |
| *A61L 27/06* | (2006.01) |
| *A61L 27/10* | (2006.01) |
| *A61L 27/24* | (2006.01) |
| *A61L 27/36* | (2006.01) |
| *A61L 27/56* | (2006.01) |

(52) U.S. Cl.
CPC .............. *A61K 38/39* (2013.01); *A61L 27/06* (2013.01); *A61L 27/10* (2013.01); *A61L 27/24* (2013.01); *A61L 27/3608* (2013.01); *A61L 27/3641* (2013.01); *A61L 27/56* (2013.01); *A61L 2430/02* (2013.01)

(58) Field of Classification Search
CPC .. C07K 14/51; C07K 14/635; C07K 2319/33; C07K 14/00
See application file for complete search history.

(56) References Cited

U.S. PATENT DOCUMENTS

| | | | | |
|---|---|---|---|---|
| 2010/0129341 A1* | 5/2010 | Sakon | ................... | C07K 14/635 424/94.6 |
| 2013/0210736 A1* | 8/2013 | Chung | .................... | A61L 27/22 514/16.7 |
| 2017/0204390 A1 | 7/2017 | Ponnapakkam et al. | | |

FOREIGN PATENT DOCUMENTS

| | | |
|---|---|---|
| JP | 07122118 A | 5/1995 |
| JP | 2010523671 A | 7/2010 |
| JP | 2013129705 A | 7/2013 |
| JP | 2015167906 A | 9/2015 |
| JP | 2015167906 A | 9/2020 |
| KR | 101183262 B1 | 9/2012 |
| KR | 1020130031870 A | 3/2013 |
| WO | 2010092135 A2 | 8/2010 |
| WO | 2011090086 A | 7/2011 |

OTHER PUBLICATIONS

Healthline. Accessed on Nov. 12, 2020 at https://www.healthline.com/health/osteogenesis-imperfecta#types (Year: 2020).*
cancer.gov. National cancer institute. Accessed on Nov. 12, 2020 at https://www.cancer.gov/types/bone/bone-fact-sheet (Year: 2020).*
Ponnapakkam, T., et al., "A Single Injection of the Anabolic Bone Agent, Parathyroid Hormone-Collagen Binding Domain (PTH-CBD), Results in Sustained Increases in Bone Mineral Density for up to 12 Months in Normal Female Mice", "Calcif. Tissue Int.", 2012, pp. 196-203, vol. 91.
Genbank, "secreted phosphoprotein 1 (osteopontin, bone sialoprotein 1, early T-lymphocyte activation 1), partial [synthetic construct]", Jul. 26, 2016, Version AAV38943.1.
Ponnapakkam, T., et al., "Monthly Administration of a Novel PTH-Collagen Binding Domain Fusion Protein is Anabolic in Mice", "Calcified Tissue International", 2011, pp. 511-520, vol. 88, Publisher: Springer Science+Business Media, LLC.
Wu, X-C, et al., "Collagen-targeting parathyroid hormone-related peptide promotess collagen binding and in vitro chondrogenesis in bone marroa-derived MSCs", "International Journal of Molecular Medicine", vol. 31, 2013, pp. 430-436.
Young, M.F., "Bone matrix proteins: their function, regulation, and relationship to osteoporosis", "Osteoporos Int.", 2003, pp. S35-S42, vol. 14, No. Suppl 3, Publisher: International Osteoporosis Foundation and national Osteoporosis Foundation.

* cited by examiner

PHARMACEUTICAL COMPOSITION AND BIOMATERIAL COMPRISING FUSION PEPTIDE IN WHICH BONE TISSUE-SELECTIVE PEPTIDE BOUND TO PARATHYROID HORMONE (PTH) OR FRAGMENT THEREOF

CROSS-REFERENCE TO RELATED APPLICATIONS

This application is a U.S. national phase under the provisions of 35 U.S.C. § 371 of International Patent Application No. PCT/KR17/13749 filed Nov. 29, 2017, which in turn claims priority of Korean Patent Application No. 10-2017-0126876 filed Sep. 29, 2017. The disclosures of International Patent Application No. PCT/KR17/13749 and Korean Patent Application No. 10-2017-0126876 are hereby incorporated herein by reference in their respective entireties, for all purposes.

TECHNICAL FIELD

The present invention relates to a pharmaceutical composition and biomaterial for preventing or treating bone diseases comprising a fusion peptide in which a bone tissue-selective peptide bound to parathyroid hormone (PTH) or a fragment thereof.

BACKGROUND

Parathyroid hormone (PTH) is a peptide hormone composed of 84 amino acids secreted from the parathyroid gland. PTH, which primarily acts on the adrenal cortex, is a physiologically active substance that binds to the adrenal cortex and increases the production of cAMP, inositol triphosphate (IP3), and diacyl glycerol (DAG). PTH increases calcium concentration in the blood by increasing absorption of calcium in the bone and kidney. In addition, PTH, which is intermittently administered, stimulates osteoblasts to induce bone formation.

Therapeutic agents for osteoporosis such as estrogen, calcitonin and bisphosphonate have a mechanism to inhibit bone resorption (osteolysis), while PTH has a mechanism to promote bone formation (osteogenesis). Drugs for inhibiting bone resorption are not sufficient to increase the bone amounts of patients with advanced osteoporosis already, but PTH has a mechanism to directly promote osteogenesis and is thus beneficial to patients with type osteoporosis with reduced bone remodeling or already advanced osteoporosis. Currently, Forteo® commercially available from Eli Lilly and Company, is known as a product approved as a therapeutic agent for osteoporosis, which uses a peptide consisting of 34 amino acids at the N-terminus among the 84 amino acids of PTH. However, Forteo® is administered by subcutaneous injection once a day due to its short half-life of 1 hour or less and thus has low patient compliance. In addition, Forteo® may cause side effects such as hypercalcemia and even a high incidence of osteosarcoma, upon use for a long time of 2 years or longer. For this reason, the use thereof for more than 2 years is prohibited.

There have been attempts to increase the stability of PTH. For example, PEG (U.S. Pat. No. 6,506,730) or albumin (WO 2010/092135) is linked to PTH to induce long circulation in blood, or amino acid is substituted to reduce the degradation by enzymes (KR 10-1183262).

In addition, there have been attempts to introduce physiologically active factors to improve bone regeneration (osteoanagenesis) and bone integration (osseointegration) of medical devices used in dentistry and orthopedics. Medical devices used in dentistry and orthopedics include bone grafts, barrier membranes, composite materials containing collagen, metal implants, screws and the like. However, since physiologically active factors are released from the surface and decomposed, the effects thereof are insufficient.

Accordingly, as a result of intensively attempted research to solve the aforementioned problems of the prior art, the present inventors developed a pharmaceutical composition and biomaterial comprising a fusion peptide in which a bone-tissue selective peptide bound to PTH or a fragment thereof, and found that the pharmaceutical composition comprising the fusion peptide is effective for the treatment of conditions requiring osteoanagenesis such as osteoporosis and fracture, and the fusion peptide is bound to the surface of a dental and orthopedic medical device and is then transplanted to increase the effect of osteoanagenesis, thereby completing the present invention.

The information disclosed in the Background section is provided only for better understanding of the background of the present invention, and it is not intended to include information creating the prior art already known to those skilled in the art.

DISCLOSURE

Technical Problem

Therefore, it is one object of the present invention to provide a pharmaceutical composition for preventing or treating bone diseases that comprises a fusion peptide with improved stability, selectivity to bone tissue and bone regeneration (osteoanagenesis) effect, as an active ingredient.

It is another object of the present invention to provide a method for preventing or treating bone diseases comprising administering a composition comprising a fusion peptide with improved stability, selectivity to bone tissue and bone regeneration effect, as an active ingredient.

It is another object of the present invention to provide the use of a composition comprising a fusion peptide with improved stability, selectivity to bone tissue and bone regeneration effect, as an active ingredient, for preventing or treating bone diseases.

It is yet another object of the present invention to provide a biomaterial in which a fusion peptide with improved stability, selectivity to bone tissue and bone regeneration effect, bound thereto.

Technical Solution

In order to achieve the foregoing objects, the present invention provides a pharmaceutical composition for preventing or treating bone diseases comprising a fusion peptide in which a bone tissue-selective peptide bound to parathyroid hormone (PTH) or a fragment thereof, as an active ingredient.

In addition, the present invention provides a method for preventing or treating bone diseases comprising administering a composition comprising a fusion peptide in which a bone tissue-selective peptide bound to parathyroid hormone (PTH) or a fragment thereof, as an active ingredient.

Further, the present invention provides the use of a composition comprising a fusion peptide in which a bone tissue-selective peptide bound to parathyroid hormone (PTH) or a fragment thereof, as an active ingredient, for preventing or treating bone diseases.

In addition, the present invention provides a biomaterial linked a fusion peptide in which a bone-tissue selective peptide bound to parathyroid hormone (PTH) or a fragment thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION AND SPECIFIC EMBODIMENTS

Figure 1:
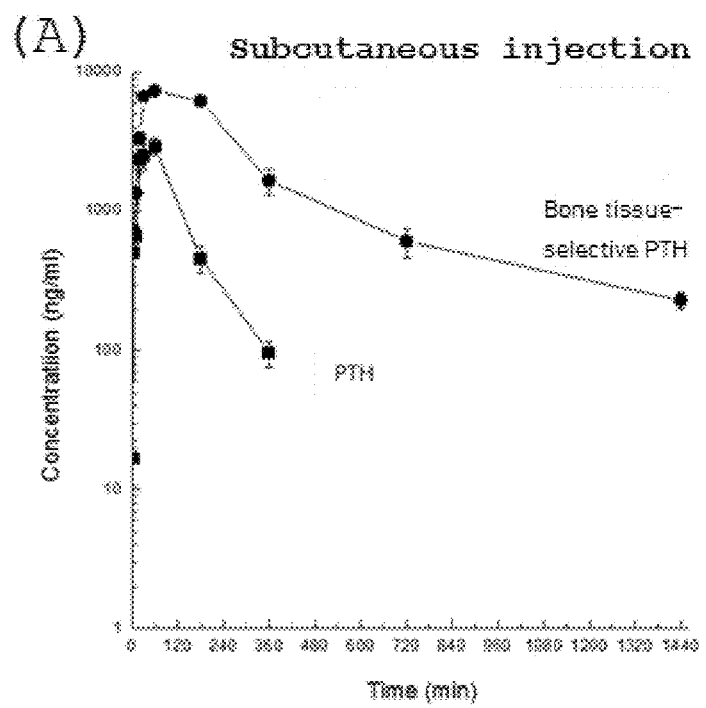
FIG. 1 is a graph showing the concentration of PTH and a fusion peptide in which a bone tissue-selective peptide bound to PTH in blood, (A) when injected intravenously and (B) when injected subcutaneously, wherein ■ represents PTH and ● represents a fusion peptide in which a bone tissue-selective peptide bound to PTH)
Figure 1:
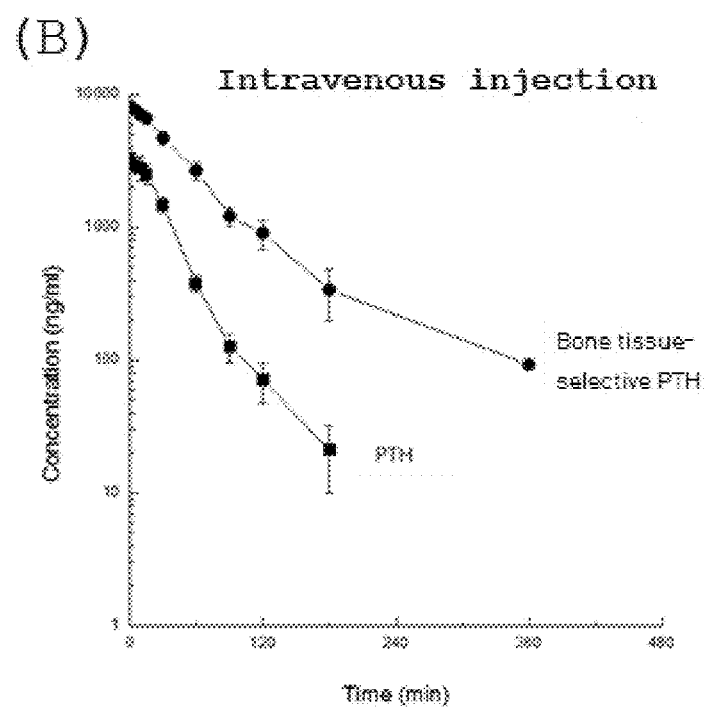

Unless defined otherwise, all technical and scientific terms used herein have the same meaning as those appreciated by those skilled in the field to which the present invention pertains. In general, nomenclature used herein is well-known in the art and is ordinarily used.

In one embodiment of the present invention, it was found that bone density was increased and bone generation effect was improved, as compared to parathyroid hormone (PTH), by injecting a pharmaceutical composition comprising a fusion peptide in which a bone tissue-selective peptide bound to parathyroid hormone (PTH) or a fragment thereof into osteoporosis-induced mice.

Accordingly, in one aspect, the present invention is directed to a pharmaceutical composition for preventing or treating bone diseases comprising a fusion peptide in which a bone tissue-selective peptide bound to parathyroid hormone (PTH) or a fragment thereof, as an active ingredient.

In another aspect, the present invention is directed to a method for preventing or treating bone diseases comprising administering a composition comprising a fusion peptide in which a bone tissue-selective peptide bound to parathyroid hormone (PTH) or a fragment thereof, as an active ingredient.

In another aspect, the present invention is directed to the use of a composition comprising a fusion peptide in which a bone tissue-selective peptide bound to parathyroid hormone (PTH) or a fragment thereof, as an active ingredient, for preventing or treating bone diseases.

According to the present invention, the fusion peptide induces formation of bone tissue.

According to the present invention, the PTH is represented by an amino acid sequence of SEQ ID NO. 4.

According to the present invention, the fragment is represented by an amino acid sequence of SEQ ID NO. 5. SEQ ID NO. 4: SVSEIQLMH NLGKHLNSME RVEWLRKKLQ DVHNFVALGA PLAPRDAGSQ RPRKKEDNVL VESHEKSLGE ADKADVNVLT KAKSQ

SEQ ID NO. 5: SVSEIQLMHNLGKHLNSMERVEWLRKKLQDVHNF

According to the present invention, the PTH or a fragment thereof may be recombinant PTH expressed in *E.coli* or yeast, or a PTH-related peptide (PTHrp) or may be produced by peptide synthesis (Hefti et al., Clinical Science, 62, 389-396(1982); Liu et al., J. Bone Miner. Res., 6: 10, 1071-1080(1991); Hock et al., J. Bone. Min. Res., 7: 1. 65-71(1992)).

According to the present invention, the bone tissue-selective peptide is represented by an amino acid sequence of SEQ ID NO. 3.

According to the present invention, the bone tissue-selective peptide is derived from bone sialoprotein I, but is not limited thereto.

According to the present invention, the peptide that imparts bone tissue-selectivity to PTH is a peptide having binding force to collagen, which is a main ingredient of bone. The bone tissue has a structure in which mineral ingredients are deposited on collagen fibers. Thus, the bone tissue-selective peptide facilities migration of PTH into bone tissue.

In one embodiment of the present invention, the peptide imparting bone tissue-selectivity used herein was separated and extracted from the amino acid sequence of the active site in proteins constituting the extracellular matrix, and was designed to maintain the active structure through chemical modification after extraction. Specifically, the peptide was required to comprise any one of YGLRSKS (SEQ ID NO. 1), KKFRRPDIQYPDAT (SEQ ID NO. 2) and YGLRSK-SKKFRRPDIQYPDAT (SEQ ID NO. 3) amino acid sequences at the positions of 149 to 169 of human bone sialoprotein I. To facilitate chemical binding to PTH, cysteine was added in the form of a CGG- or CGGGGG-spacer to the N-terminus of the amino acid sequence selected from the amino acid sequences listed above and was chemically synthesized to prepare the peptide.

According to the present invention, the fusion peptide may have a structure in which the N-terminus of the bone tissue-selective peptide is bound to the C-terminus of PTH or a fragment thereof.

The bone tissue-selective peptide may be bound to the C-terminus of PTH or a fragment thereof by solid phase peptide synthesis or with the use of a chemical crosslinking agent, but the present invention is not limited thereto.

According to the present invention, a chemical crosslinking agent may be used to link the N-terminus of the bone tissue-selective peptide to the C-terminus of PTH or a fragment thereof. In this case, a functional group capable of binding to the cysteine at the terminal of the peptide, for example, an SH group can be introduced, or treatment can be performed to form amine ($NH_2$), thereby facilitating the subsequent cross-linking reaction using a crosslinking agent.

The chemical crosslinking agent may be selected from the group consisting of 1,4-bis-maleimidobutane (BMB), 1,11-bis-maleimidotetraethyleneglycol (BM[PEO]$_4$), 1-ethyl-3-[3-dimethyl aminopropyl] carbodiimide hydrochloride (EDC), succinimidyl-4-[N-maleimidomethylcyclohexane-1-carboxy-[6-amidocaproate]] (SMCC) and sulfonates thereof (sulfo-SMCC), succinimidyl 6-[3-(2-pyridyldithio)-propionamido] hexanoate] (SPDP) and sulfonates thereof (sulfo-SPDP), m-maleimidobenzoyl-N-hydroxysuccinimide ester (MBS) and sulfonates thereof (sulfo-MBS), succinimidyl [4-(p-maleimidophenyl) butyrate] (SMPB) and sulfonates thereof (sulfo-SMPB), but the present invention is not limited thereto.

In order to remove the crosslinking agent after binding of PTH to the bone tissue-selective peptide, the fusion peptide in which a bone tissue-selective peptide bound to PTH is subjected to purification such as ultrafiltration so that the fusion peptide in which a bone tissue-selective peptide bound to PTH has a purity of 90% or more, more preferably, 98% or more.

In the present invention, the bone disease is selected from the group consisting of osteoporosis, osteogenesis imperfecta, hypercalcemia, osteomalacia, Paget's disease, bone loss and osteonecrosis due to cancer, osteoarthritis, rheumatoid arthritis, periodontal disease and fracture, but is not limited thereto.

In the present invention, the pharmaceutical composition for preventing or treating bone diseases may be formulated for intravenous, intraperitoneal, intramuscular, intraarterial, oral, paradental, intracardial, intramedullary, intrathecal, transdermal, intestinal, subcutaneous, sublingual or topical administration, but is not limited thereto.

In the present invention, the pharmaceutical composition for preventing or treating bone diseases is formulated into any one selected from the group consisting of injections, oral mucosal agents, capsules, films, patches, percutaneous agents and gels, but is not limited thereto. The pharmaceutical composition may be administered via topical, subcutaneous, intravenous, or parenteral routes. In general, the pharmaceutical composition may contain a therapeutically effective amount of the fusion peptide in which a bone-tissue selective peptide bound to PTH or a fragment thereof, as an active ingredient, according to the present invention.

In the present invention, the pharmaceutical composition may be prepared by a well-known method using a pharmaceutically acceptable inert inorganic or organic excipient. Examples of the excipient for preparing injections include, but are not limited to, water, alcohols, glycerol, polyols, vegetable oils and the like. Alternatively, the injection may be used in combination with a preservative, an analgesic agent, a solubilizer and a stabilizer. The topical formulation may be prepared in the form of a gel or film and the main ingredient of the gel is preferably collagen, chitosan, hyaluronic acid, alginic acid, propylene glycol, propylene glycol alginate, poloxamer, chondroitin sulfate or the like.

In the present invention, the content of the fusion peptide in the pharmaceutical composition may be 10 to 100 μg. The pharmaceutical composition may be formulated into a single subcutaneous or intravenous injection containing a dose of 10 to 100 μg of the fusion peptide in which a bone-tissue selective peptide bound to PTH or a fragment thereof.

In one embodiment of the present invention, the effect of bone regeneration can be identified using a bone implant linked the fusion peptide in which a bone-tissue selective peptide bound to PTH or a fragment thereof.

In another aspect, the present invention is directed to a biomaterial linked the fusion peptide in which a bone-tissue selective peptide bound to parathyroid hormone (PTH) or a fragment thereof.

According to the present invention, the fusion peptide induces formation of bone tissue.

According to the present invention, the PTH is represented by an amino acid sequence of SEQ ID NO. 4.

According to the present invention, the fragment is represented by an amino acid sequence of SEQ ID NO. 5.

According to the present invention, the bone tissue-selective peptide is represented by an amino acid sequence of SEQ ID NO. 3.

According to the present invention, the bone-tissue selective peptide has a structure in which the N-terminus of the bone tissue-selective peptide is bound to the C-terminus of PTH or a fragment thereof.

The bone tissue-selective peptide may be bound to the C-terminus of PTH or a fragment thereof by a crosslinking agent. The crosslinking agent may be selected from the group consisting of 1,4-bis-maleimidobutane (BMB), 1,11-bis-maleimidotetraethyleneglycol (BM[PEO]$_4$), 1-ethyl-3-[3-dimethyl aminopropyl] carbodiimide hydrochloride (EDC), succinimidyl-4-[N-maleimidomethylcyclohexane-1-carboxy-[6-amidocaproate]](SMCC) and sulfonates thereof (sulfo-SMCC), succinimidyl 6-[3-(2-pyridyldithio)-propionamido] hexanoate](SPDP) and sulfonates thereof (sulfo-SPDP), m-maleimidobenzoyl-N-hydroxysuccinimide ester (MBS) and sulfonates thereof (sulfo-MBS), succinimidyl [4-(p-maleimidophenyl) butyrate] (SMPB) and sulfonates thereof (sulfo-SMPB), but the present invention is not limited thereto.

According to the present invention, the biomaterial may be any one selected from the group consisting of bone grafts, barrier membranes, implants and polymer scaffolds.

The biomaterial may include all kinds and types of bone grafts, barrier membranes, implants and polymer scaffolds.

The bone graft comprises, as a main ingredient, an organism-derived bone-mineral powder derived from autogenous bone, bovine bone and porcine bone, and a porous block thereof, a synthetic hydroxyapatite powder and a porous block thereof, a tricalcium phosphate powder and a porous block thereof, or a mixture of hydroxyapatite and tricalcium phosphate powders, and a porous block thereof.

The barrier membrane is preferably produced from collagen, chitosan, gelatin, polylactide, polylactide glycolide or polycaprolactone, but is not limited thereto.

The implant may be produced from titanium alloy, titanium oxide or zirconia, but the present invention is not limited thereto. The implant may include dental and orthopedic implants. The orthopedic implants include orthopedic fixation plates, orthopedic bone screws, orthopedic bone nails, and the like.

In the present invention, the fusion peptide may be present in an amount of 1 to 10 mg with respect to the unit weight (1 g) of the biomaterial. More preferably, the fusion peptide may be present in an amount of 2 to 8 mg with respect to the unit weight (1 g) of the biomaterial.

EXAMPLE

Hereinafter, the present invention will be described in more detail with reference to examples. However, it is obvious to those skilled in the art that these examples are provided only for illustration of the present invention and should not be construed as limiting the scope of the present invention.

Preparation Example 1

Preparation of Fusion Peptide in Which Bone Tissue-Selective Peptide Bound to PTH by Solid Phase Peptide Synthesis The peptide was synthesized using F-moc solid phase chemical synthesis by connecting a bone tissue-selective peptide (SEQ ID NO. 3) and a PTH fragment (SEQ ID NO. 5) in order from the N-terminus. The synthesized peptide sequence was cleaved from a resin, washed, lyophilized, and then separated and purified by liquid chromatography. The molecular weight of the purified peptide was identified by MALDI-TOF assay.

Comparative Example 1

Preparation of PTH Fragment

The peptide was synthesized using F-moc solid phase chemical synthesis by connecting a PTH fragment (SEQ ID NO. 5). The synthesized peptide sequence was cleaved from a resin, washed, lyophilized, and then separated and purified by liquid chromatography. The molecular weight of the purified peptide was identified by MALDI-TOF assay.

Preparation Example 2

Preparation of Fusion Peptide in Which Bone Tissue-Selective Peptide Bound to PTH by Crosslinking Reaction 1 mg of the PTH fragment (SEQ ID NO. 5) was dissolved in 1 ml of a conjugation reaction buffer (100 mM sodium phosphate, 150 mM sodium chloride, 0.02% sodium azide, 1 mM EDTA). 40 µl of a Sulfo-SMCC (Thermo Scientific, 4.8 mg/ml) solution was added portionwise to PTH in small amounts and reacted in the absence of light at room temperature for 1 or hours. The unreacted sulfo-SMCC was removed by ultrafiltration through a membrane with a molecular weight cut-off of 500 kDa. A solution (1 mg/ml) of the peptide of SEQ ID NO. 3 in a conjugation buffer was added thereto and the resulting mixture was reacted in the absence of light for 4 to 8 hours. The fusion peptide comprising the bone tissue-selective peptide bound to PTH was subjected to ultrafiltration through a membrane with a molecular weight cut-off of 3,000 kDa to remove the unreacted peptide of SEQ ID NO. 3. Using MALDI-TOF and SDS-PAGE, the molecular weight of the fusion peptide in which a bone tissue-selective peptide bound to PTH was identified. The theoretical molecular weight should be at least 6,701.89 kDa, when taking into consideration the fact that the molecular weight of the PTH fragment is 4,117.8 kDa, the molecular weight of the bone tissue-selective peptide is 2,365 kDa, and the molecular weight increased by Sulfo-SMCC is 219.09 kDa.

Preparation Example 3

Preparation of Pharmaceutical Composition Comprising Fusion Peptide in which Bone Tissue-Selective Peptide Bound to PTH A pharmaceutical composition comprising the fusion peptide in which the bone tissue-selective peptide bound to PTH of Preparation Example 2 as an active ingredient was prepared (Table 1).

TABLE 1

Pharmaceutical composition of Preparation Example 3

| Ingredient | Weight (mg) |
|---|---|
| Fusion peptide in which bone tissue-selective peptide bound to PTH | 1 |
| Sodium chloride, USP | 8.18 |
| Sodium succinate | 1.62 |
| WFI | 987.5 |
| Sodium hydroxide, NF and/or acetic acid, NF | |
| Total | 1 g, pH 6 |

Comparative Example 2

Preparation of Pharmaceutical Composition Comprising PTH

A pharmaceutical composition comprising the PTH of Comparative Example 1 as an active ingredient was prepared (Table 2).

TABLE 2

Pharmaceutical composition of Comparative Example 2

| Ingredient | Weight (mg) |
|---|---|
| PTH | 1 |
| Sodium chloride, USP | 8.18 |
| Sodium succinate | 1.62 |
| WFI | 987.5 |
| Sodium hydroxide, NF and/or acetic acid, NF | |
| Total | 1 g, pH 6 |

Preparation Example 4

Preparation of Bone Graft Linked Fusion Peptide in Which Bone Tissue-Selective Peptide Bound to PTH 1 g of a bovine bone-derived bone graft was allowed to stand in 3-aminopropyl ethoxysilane (APTES, 1%) dissolved in hexane and then washed three times with hexane. As a result, an amine residue was formed on the surface and BMB as a crosslinking agent was added thereto. 1 g of the bone graft particles bound to the crosslinking agent were reacted with 20 mg of the fusion peptide in which a bone tissue-selective peptide bound to PTH of Preparation Example 2 for 12 hours, washed 3 times with methanol and then washed 10 times with purified water, to obtain a bone graft which the fusion peptide in which a bone tissue-selective peptide bound to PTH is fixed.

Comparative Example 3

Preparation of Bone Graft Comprising PTH Linked Thereto 1 g of a bovine bone-derived bone graft was allowed to stand in 3-aminopropyl ethoxysilane (APTES, 1%) dissolved in hexane and then washed three times with hexane. As a result, an amine residue was formed on the surface and BMB as a crosslinking agent was added thereto. 1 g of the bone graft particles bound to the crosslinking agent was reacted with 20 mg of the PTH of Comparative Example 1 for 12 hours, washed 3 times with methanol and then washed 10 times with purified water to obtain a bone graft to which the PTH is fixed.

Preparation Example 5

Preparation of Gel-Type Composition of Fusion Peptide in Which Bone Tissue-Selective Peptide Bound to PTH 20 mg of the fusion peptide in which bone tissue-selective peptide bound to PTH of Preparation Example 2 was homogeneously mixed with 1 ml of a 2% collagen solution and a syringe was filled with the resulting mixture.

Comparative Example 4

Preparation of Gel-Type Composition of PTH 20 mg of the PTH of Comparative Example 1 was homogeneously mixed with 1 ml of a 1 to 3% collagen solution and a syringe was filled with the resulting mixture.

Example 1

Test for Determining Half-Life of Fusion Peptide in Which Bone Tissue-Selective Peptide Bound to PTH A composition comprising the PTH of Comparative Example 2 and a composition comprising the fusion peptide in which a bone tissue-selective peptide bound to PTH of Preparation Example 3 were subcutaneously administered at a concentration of 100 μg/kg to SD (Sprague-Dawley) male rats (body weight 300-350g) and blood was collected at 0, 2, 5, 10, 20, 30, 60, 180, 360, 720, and 1,440 minutes. In addition, the compositions were injected at a concentration of 100 μg/kg into the jugular vein, blood was collected at 0, 5, 10, 15, 30, 60, 90, 120, 180 and 360 minutes, and the plasma was separated by centrifugation at 14,000 rpm for 10 minutes. The concentration of PTH was measured by enzyme-linked immunosorbent assay (ELISA) (Immutopics, Inc., San Clemente, Calif.).

FIG. 1 shows the concentration of the fusion peptide in which a bone tissue-selective peptide bound to PTH in blood over time. When subcutaneously injected, PTH was not detected after 360 minutes, but the fusion peptide in which a bone tissue-selective peptide bound to PTH was detected at up to 1,440 minutes. In the case of intravenous injection, PTH was not measured after 180 minutes, but the fusion peptide in which a bone tissue-selective peptide bound to PTH was measured up to at 360 minutes. This means that the half-life of the fusion peptide in which a bone tissue-selective peptide bound to PTH is longer than that of PTH.

Example 2

Efficacy Test of Fusion Peptide in Qhich Bone Tissue-Selective Peptide to PTH in Osteoporosis Animal Six week-old ICR mice were anesthetized by intramuscular injection using a mixture of 10 mg/kg of xylazine (Rompun®, Bayer, Korea) and 100 mg/kg of ketamine (Ketalar®, Yuhan Co., Ltd., Korea) and then the ovaries present below the bilateral kidneys were entirely removed carefully. Suturing was performed by an ordinary method and 3 mg/kg of gentamicin (Gentamycin®, JW Pharmaceutical Corporation, Korea) was intramuscularly injected.

Three months after the ovariectomy, whether or not bone loss occurred was checked. The pharmaceutical composition comprising PTH of Comparative Example 2 was administered at 20 μg/kg daily for 3 months, and the pharmaceutical composition comprising the fusion peptide in which a bone tissue-selective peptide bound to PTH of Preparation Example 3 was administered at 80 pg/kg weekly for 6 months. The change in bone density was evaluated, as compared with a group not treated with osteoporosis.

Figure 2:
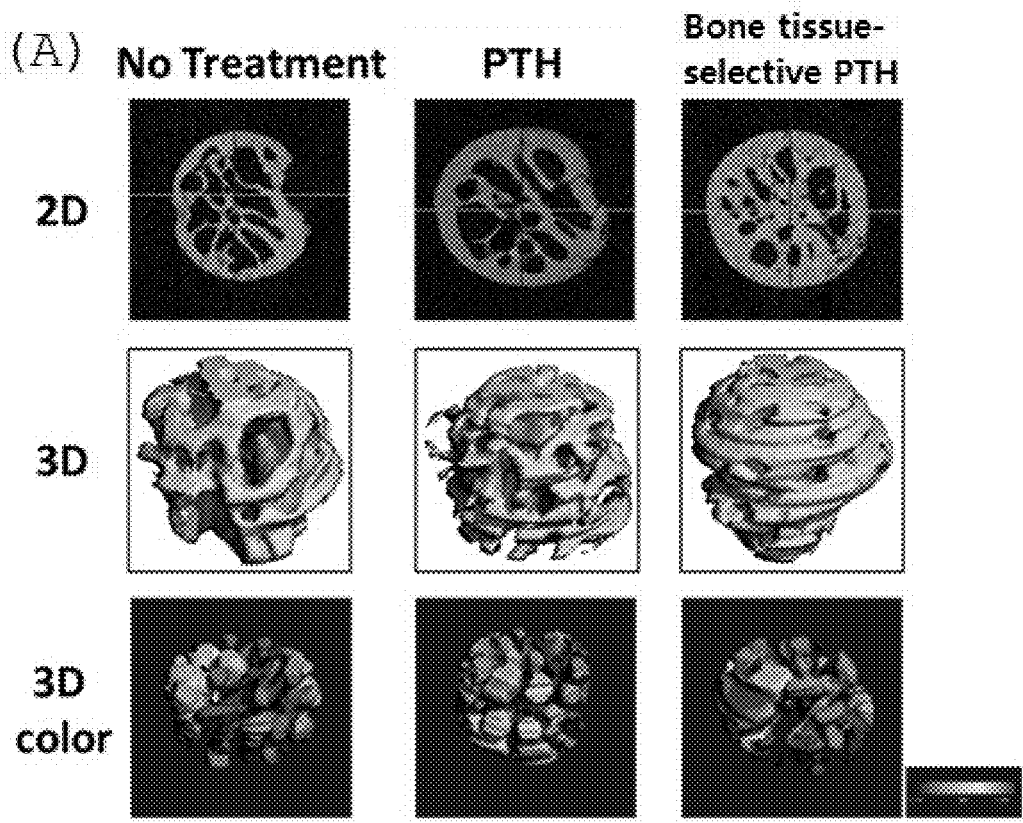
FIG. 2 is a microCT image of the femur of osteoporosis-induced mice (A), and shows results of measurement of bone mineral density (BMD) (B), after injection of PTH and a fusion peptide in which a bone tissue-selective peptide bound to PTH into the osteoporosis-induced mice, wherein ■ represents no treatment, ● represents PTH and ▲ represents a fusion peptide in which a bone tissue-selective peptide bound to PTH)
Figure 2:
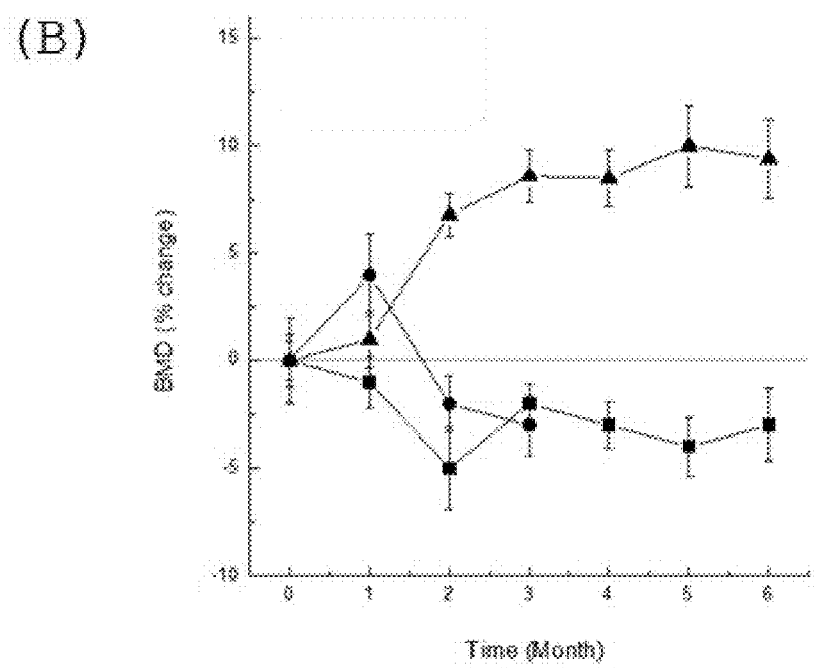

FIG. 2 shows a microCT image and measurement results of bone mineral density (BMD) of the femur after injection of the fusion peptide comprising a bone tissue-selective peptide bound to PTH into osteoporosis-induced mice. In the group with no treatment after ovariectomy, bone density was reduced due to significant bone loss. The group treated with the fusion peptide in which a bone tissue-selective peptide bound to PTH showed an increase in bone density, as compared to the group treated with PTH (FIG. 2(A)). As a result of measurement of variation in BMD (bone mineral density), meaning the total mineral content in the femoral head (FIG. 2(B)), the variation in BMD in the group with no treatment after ovariectomy was found to be decreased. The group treated with PTH showed an increase in BMD variation at up to one month and a decrease starting at two months. The fusion peptide in which a bone tissue-selective peptide bound to PTH showed an increase in BMD at up to 6 months. This means that the fusion peptide in which a bone tissue-selective peptide bound to PTH is much more effective in bone regeneration than PTH.

Figure 3:
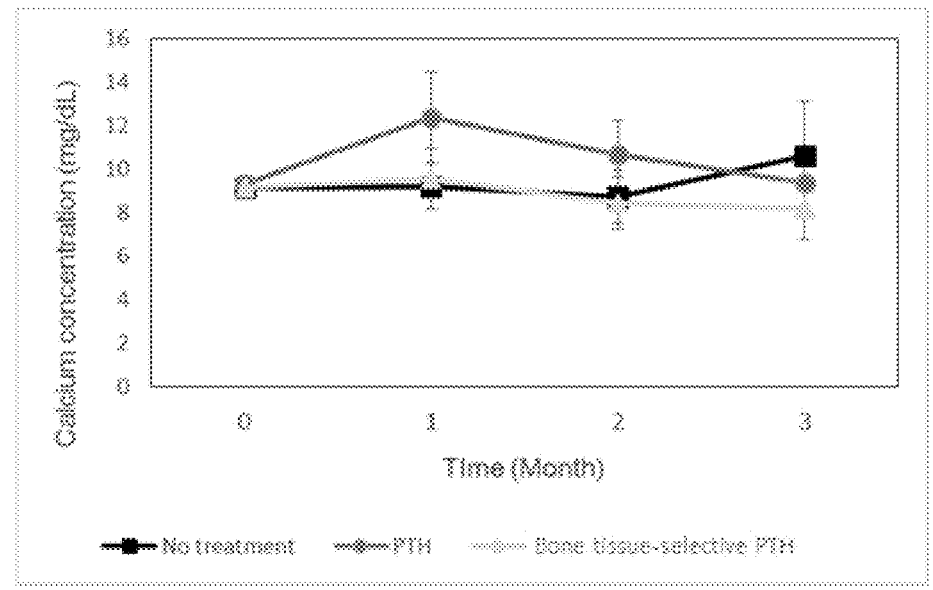
FIG. 3 is a result of measurement of calcium concentration in blood after injection of PTH and a fusion peptide in which a bone tissue-selective peptide bound to PTH into osteoporosis-induced mice, wherein ■ represents no treatment, ● represents PTH and ▲ represents a fusion peptide in which a bone tissue-selective peptide bound to PTH)

FIG. 3 shows the result of measurement of the concentration of calcium in blood after injection of the fusion peptide in which a bone tissue-selective peptide bound to PTH into osteoporosis-induced mice. The concentration of calcium in blood was determined using a QuantiChrom™ calcium assay kit (Bioassay Systems, Hayward, Calif.). PTH increased the concentration of calcium at one month, but the fusion peptide in which a bone tissue-selective peptide bound to PTH did not increase the concentration of calcium in blood. One of the effects of PTH on the human body is to increase the concentration of calcium in blood by affecting bones and kidneys. Therefore, long-term administration of PTH causes side effects that induce hypercalcemia. However, it was confirmed that the fusion peptide in which a bone tissue-selective peptide bound to PTH did not act to increase the concentration of calcium in blood, because it affected only bone tissue, not affecting the kidneys.

Example 3

Test for Bone Regeneration of Fusion Peptide in Which Bone Tissue-Selective Peptide Bound to PTH A circular bone defect site having a diameter of 10 mm was formed in the skull region of anesthetized rabbits (New Zealand white rabbit, cuniculus) and 100 mg of the bone graft prepared in Preparation Example 4 and Comparative Example 3 were transplanted into the bone defect site. The periosteum and the skin were double-sutured. Animals were sacrificed 3 weeks after transplantation, the collected specimens were fixed in a formalin solution, and the tissue was embedded to produce samples with a thickness of 20 μm. The prepared samples were stained with hematoxylin-eosin to prepare undecalcified specimens. The prepared specimens were observed with an optical microscope and imaged.

Figure 4:
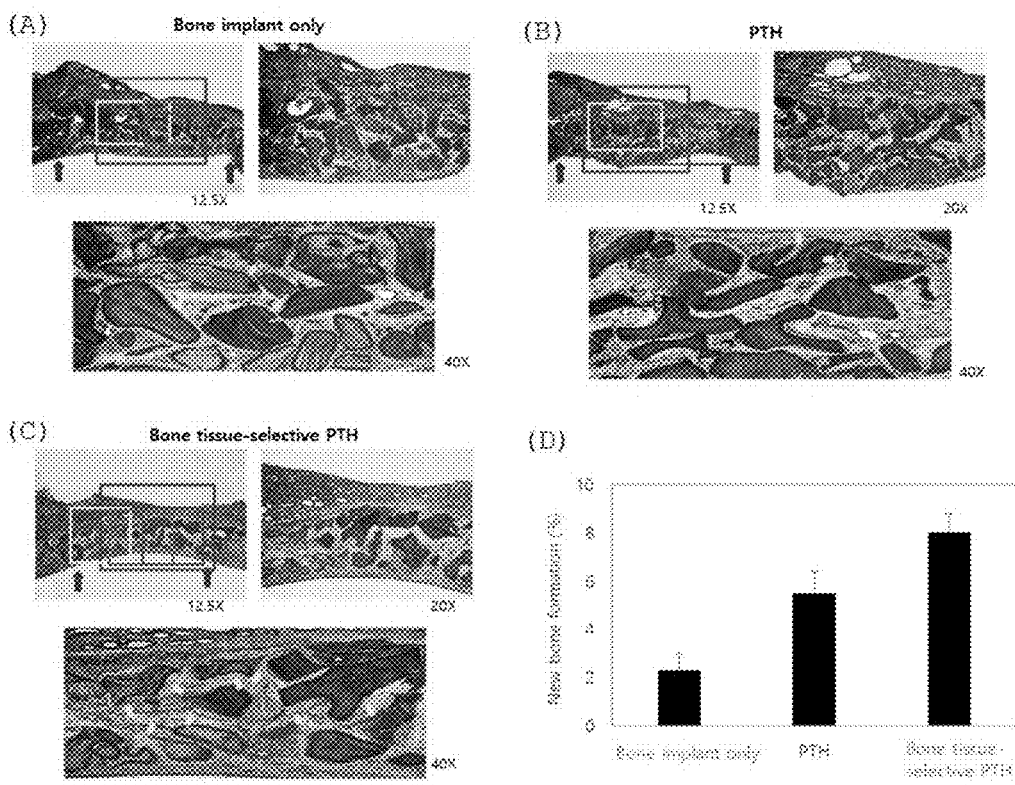
FIG. 4 shows results of histological and histomorphometric observation regarding new bone after transplanting a bone graft comprising PTH and a fusion peptide in which a bone tissue-selective peptide bound to PTH into a rabbit skull.

FIG. 4 shows results of histological and histomorphometric observation regarding new bones after transplanting a bone graft comprising the fusion peptide in which a bone tissue-selective peptide bound PTH into a rabbit skull. The bone regeneration effect of the fusion peptide in which a bone tissue-selective peptide bound to PTH was increased more than PTH. Therefore, it is expected that the bone graft having a surface linked the fusion peptide in which a bone tissue-selective peptide bound to PTH is more effective in bone regeneration than the bone graft to which PTH binds.

Example 4

Bone Migration Test for PTH and Fusion Peptide in Which Bone Tissue-Selective Peptide Bound to PTH Cyanine 5.5 was bound to the fusion peptide in which a bone tissue-selective peptide bound to PTH of Preparation Example 2, and unreacted cyanine 5.5 was removed. The cyanine 5.5-labeled fusion peptide in which a bone tissue-selective peptide bound to PTH was prepared by the method in accordance with Preparation Example 5. The PTH of Comparative Example 1 was bound to cyanine 5.5 and unreacted cyanine 5.5 was removed. As a control group, cyanine 5.5-labeled PTH was prepared in accordance with the method of Comparative Example 4.

An implant was transplanted 8 weeks after extraction of the teeth of beagles, and 100 µL of a collagen gel comprising the cyanine 5.5-labeled fusion peptide in which a bone tissue-selective peptide bound to PTH was injected into the surgical site and sutured. Animals were sacrificed 3 weeks after transplantation, the collected specimens were fixed in a formalin solution and tissues were embedded to prepare specimens with a thickness of 20 µm. The prepared specimens were stained with hematoxylin-eosin to prepare undecalcified specimens. The prepared specimens were observed with a confocal microscopy and imaged. The fluorescent intensity per a predetermined unit area near the implant was measured.

Figure 5:
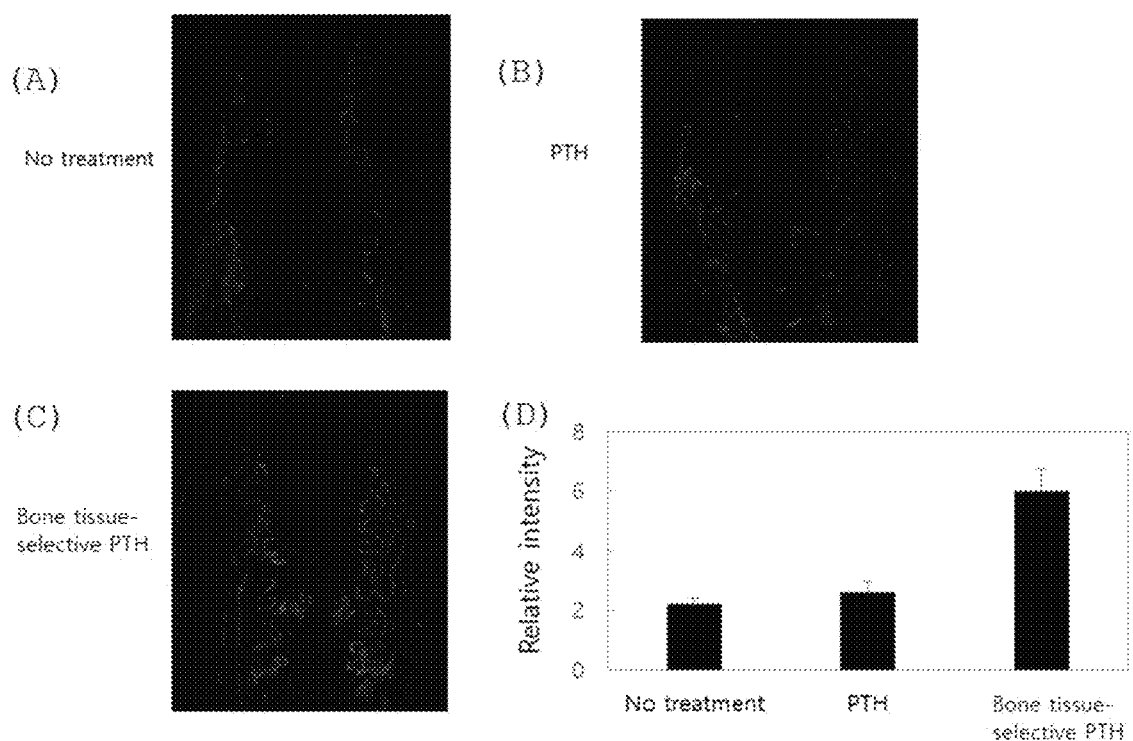
FIG. 5 shows the distribution of a bone tissue near an implant of fluorescence-labeled PTH and fluorescence-labeled fusion peptide in which a bone tissue-selective peptide bound to PTH.

FIG. 5 shows the distribution of a bone tissue near an implant of the fluorescence-labeled fusion peptide in which a bone tissue-selective peptide bound to PTH. When the PTH was transplanted, there was almost no fluorescence in the surrounding bone tissue. However, in the case of the fusion peptide in which a bone tissue-selective peptide bound to PTH, fluorescence distributed in the surrounding bone tissue was observed. This indicates that the fusion peptide in which a bone tissue-selective peptide bound to PTH selectively binds to bone tissue, as compared to PTH.

INDUSTRIAL APPLICABILITY

According to the present invention, it is possible to increase the selectivity to bone tissue and to increase the bone regeneration effect by introducing a peptide having selectivity to bone tissue into PTH or a fragment thereof. In addition, the peptide can be developed into pharmaceutical compositions for preventing or treating bone diseases, which can improve patient compliance, by increasing the half-life of PTH and consequently increasing the interval of administration. Further, the present invention is useful for further improving bone regeneration effects by applying PTH bound to a bone tissue-selective peptide to biomaterials for dentistry and orthopedics.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

The invention claimed is:

1. A method for treating osteoporosis by selectively distributing a fusion peptide to bone tissue, comprising administering (i) the fusion peptide in which a bone tissue-selective peptide represented by an amino acid sequence of SEQ ID NO: 3 bound to parathyroid hormone (PTH) or a fragment thereof, as an active ingredient; or (ii) a composition comprising said fusion peptide, wherein the content of the fusion peptide in the composition is 10 to 100 μg.

2. The method for treating osteoporosis according to claim 1, wherein the fusion peptide induces formation of bone tissue.

3. The method for treating osteoporosis according to claim 1, wherein the parathyroid hormone (PTH) is represented by an amino acid sequence of SEQ ID NO. 4.

4. The method for treating osteoporosis according to claim 1, wherein the fragment is represented by an amino acid sequence of SEQ ID NO. 5.

5. The method for treating osteoporosis according to claim 1, wherein the bone tissue-selective peptide is derived from bone sialoprotein I.

6. The method for treating osteoporosis according to claim 1, wherein the fusion peptide has a structure in which the N-terminus of the bone tissue-selective peptide is bound to a C-terminus of parathyroid hormone (PTH) or a fragment thereof.

7. The method for treating osteoporosis according to claim 1, wherein the composition is formulated for intravenous, intraperitoneal, intramuscular, intraarterial, oral, paradental, intracardial, intramedullary, intrathecal, transdermal, intestinal, subcutaneous, sublingual or topical administration.

8. The method for treating osteoporosis according to claim 1, wherein the composition is formulated into any one selected from the group consisting of injections, oral mucosal agents, capsules, films, patches, percutaneous agents and gels.

* * * * *

UNITED STATES PATENT AND TRADEMARK OFFICE
CERTIFICATE OF CORRECTION

PATENT NO. : 11,179,445 B2  
APPLICATION NO. : 16/326210  
DATED : November 23, 2021  
INVENTOR(S) : Yoon Jeong Park et al.

Page 1 of 1

It is certified that error appears in the above-identified patent and that said Letters Patent is hereby corrected as shown below:

In the Specification

Column 9, Line 58, "Qhich" should be -- Which --.

Column 10, Line 9, "80 pg/kg" should be -- 80 μg/kg --.

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: bone sialoprotein I

<400> SEQUENCE: 1

Tyr Gly Leu Arg Ser Lys Ser
1               5

<210> SEQ ID NO 2
<211> LENGTH: 14
<212> TYPE: PRT
<213> ORGANISM: Artificial Sequence
<220> FEATURE:
<223> OTHER INFORMATION: bone sialoprotein I

<400> SEQUENCE: 2

Lys Lys Phe Arg Arg Pro Asp Ile Gln Tyr Pro Asp Ala Thr
1               5                   10

<210> SEQ ID NO 3
<211> LENGTH: 21
<212> TYPE: PRT
<213> ORGANISM: Artificial Sequence
```

```
<220> FEATURE:
<223> OTHER INFORMATION: bone sialoprotein I

<400> SEQUENCE: 3

Tyr Gly Leu Arg Ser Lys Ser Lys Lys Phe Arg Arg Pro Asp Ile Gln
1               5                   10                  15

Tyr Pro Asp Ala Thr
            20

<210> SEQ ID NO 4
<211> LENGTH: 84
<212> TYPE: PRT
<213> ORGANISM: Artificial Sequence
<220> FEATURE:
<223> OTHER INFORMATION: PTH

<400> SEQUENCE: 4

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 5
<211> LENGTH: 34
<212> TYPE: PRT
<213> ORGANISM: Artificial Sequence
<220> FEATURE:
<223> OTHER INFORMATION: PTH

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```